US012380969B2

(12) United States Patent
Jandhyala et al.

(10) Patent No.: US 12,380,969 B2
(45) Date of Patent: Aug. 5, 2025

(54) DESIGNING CEMENT THAT WITHSTANDS PERFORATIONS AND OTHER IMPACT LOADS

(71) Applicant: Halliburton Energy Services, Inc., Houston, TX (US)

(72) Inventors: Siva Rama Krishna Jandhyala, The Woodlands, TX (US); Thomas Jason Pisklak, Houston, TX (US); Ronnie Glen Morgan, Duncan, OK (US); John Paul Bir Singh, Kingwood, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 904 days.

(21) Appl. No.: 17/550,767

(22) Filed: Dec. 14, 2021

(65) Prior Publication Data
US 2023/0187029 A1 Jun. 15, 2023

(51) Int. Cl.
*G16C 20/30* (2019.01)
*C09K 8/46* (2006.01)
*G16C 20/70* (2019.01)

(52) U.S. Cl.
CPC .............. *G16C 20/30* (2019.02); *C09K 8/46* (2013.01); *G16C 20/70* (2019.02)

(58) Field of Classification Search
CPC ............ G16C 20/30; G16C 20/70; C09K 8/46
See application file for complete search history.

(56) References Cited

U.S. PATENT DOCUMENTS

2013/0105162 A1   5/2013   Abad et al.
2015/0321953 A1 * 11/2015   Porcherie .............. C04B 28/04
                                                  106/713
(Continued)

FOREIGN PATENT DOCUMENTS

CN   111517703         8/2020
CN   111620608 A *     9/2020   ............ C04B 28/00
(Continued)

OTHER PUBLICATIONS

International Search Report and Written Opinion for PCT/US2022/041905 dated Dec. 21, 2022.
(Continued)

*Primary Examiner* — Crystal J Lee
(74) *Attorney, Agent, or Firm* — Thomas Rooney; C. Tumey Law Group PLLC

(57) ABSTRACT

The invention is directed to a method for designing cement slurry compositions based on toughness. The method addresses the problem of achieving a cement slurry with a desired toughness by iteratively selecting a cementitious material and water, including their concentrations, to form a cement slurry recipe. A toughness model, utilizing physico-chemical properties of the recipe components, calculates the toughness of the slurry. The calculated toughness is compared to a predetermined toughness requirement. If the requirement is not met, the selection process is repeated with different materials or concentrations until the toughness requirement is satisfied. The resulting cement slurry recipe is used to prepare a cement slurry suitable for applications requiring specific toughness characteristics such as in wellbore cementing.

18 Claims, 6 Drawing Sheets

(56) References Cited

U.S. PATENT DOCUMENTS

| | | | | |
|---|---|---|---|---|
| 2017/0364607 A1 * | 12/2017 | Kaushik | .................. | C09K 8/00 |
| 2019/0144734 A1 * | 5/2019 | Terrier | ..................... | C09K 8/48 |
| | | | | 166/293 |

FOREIGN PATENT DOCUMENTS

| | | | | |
|---|---|---|---|---|
| EP | 2876145 | | 5/2015 | |
| EP | 2876145 A1 * | | 5/2015 | ............. C04B 28/04 |
| WO | WO-2018156123 A1 * | | 8/2018 | ............. C04B 18/08 |
| WO | 2020204958 A1 | | 10/2020 | |

OTHER PUBLICATIONS

Golewski, Grzegorz (2017). Generalized Fracture Toughness and Compressive Strength of Sustainable Concrete Including Low Calcium Fly Ash. Materials, 10(12), 1393.

Mohammad A. Mosaberpanah, et al., Computers and Concrete, vol. 17, No. 4, Apr. 2016, pp. 477-488. Abstract.

* cited by examiner

DESIGNING CEMENT THAT WITHSTANDS PERFORATIONS AND OTHER IMPACT LOADS

BACKGROUND

Annular cement sheaths or plugs set in oil wells are sometimes subjected to high intensity force loads within a short period of time. Such loads may be called impact loads. For example, during perforation operations, a high-intensity localized force may be exerted over a short period of time. Shock waves that are generated during this event may propagate over long distances. If the designed cement does not have adequate fracture toughness, this propagation may result in unwanted fractures beyond their intended impact site. These unwanted fractures may include, but not be limited to, fractures along a cement sheath in a direction perpendicular (axial) to the radial direction of an intended perforation force vector. These axial fractures can allow one fracture stage to communicate with another fracture stage, thus reducing the effectiveness and efficiency of multiple stage fracturing processes.

BRIEF DESCRIPTION OF THE DRAWINGS

These drawings illustrate certain aspects of some examples of the present invention and should not be used to limit or define the invention.

DETAILED DESCRIPTION

Figure 1:
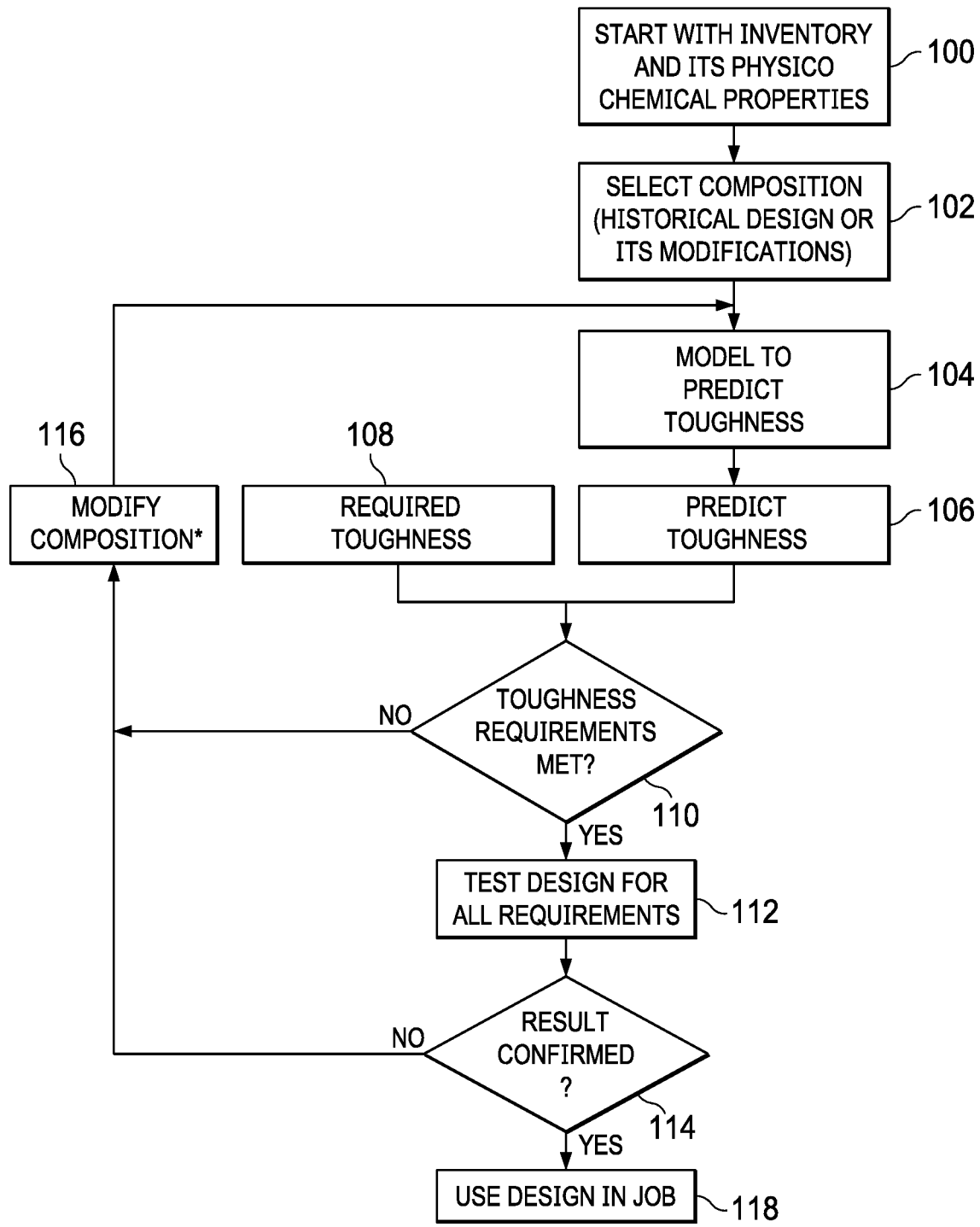
FIG. 1 illustrates an exemplary method to determine a toughness value for a composition based on physico-chemical properties of the composition and test conditions, in accordance with particular examples of the present disclosure.

Systems and methods of the present disclosure relate to assessing an existing composition and/or designing a new composition for a target toughness value. In particular examples, the toughness value may be determined by using a mathematical model that may determine the toughness value based on physico-chemical properties of the composition and test conditions. In some examples, the composition may be used as a recipe to design and produce a cement slurry.

Cement slurries may include cement components such as cement, supplementary cementitious additives, inert materials, and chemical additives, for example. Cement slurry recipes, sometimes referred to as a cement design or other equivalent names thereof, may be unique to each well to satisfy the differing design requirements for each well. Cement slurry recipes may be developed such that a cement slurry prepared from the cement slurry recipe meets the design requirements for a cement slurry such as viscosity, density, and rheology, for example, and that a set cement resulting from the setting of the cement slurry meets all the design requirements such as toughness value, compressive strength, tensile strength, Young's modulus, for example. When the cement slurry recipe is developed, representative samples of cement slurry may be prepared and tested in a laboratory to verify that the cement slurry and set cement have the required physical properties. Toughness of a set cement prepared from the cement slurry recipe may be measured in a laboratory using a laboratory equipment. Once a cement slurry recipe is verified as meeting the design requirements, the cement slurry recipe may be selected for preparation and the prepared slurry may be introduced into a wellbore. A cement slurry for use in cementing wellbores is typically mixed at a wellbore pad site using cement mixing equipment and pumped into the wellbore using cement pumps.

For example, when a cement sheath is subjected to loading, it accumulates energy and may fracture at a threshold. The threshold for fracturing may be indicated by toughness. Non-limiting examples of the toughness may include fracture toughness, sudden impact toughness (e.g., due to perforations), or compressive strength toughness, and secant toughness.

Mathematically, the toughness may be related to the area under a stress-strain curve. In some examples, the secant toughness index may be equal to the total strain to failure divided by elastic strain. Impact toughness is the amount of energy absorbed in the fracture of the material. It is measured as a difference in potential energy of a pendulum between the start and end of the test. The pendulum impacts the material during the test. The variations in relative toughness of a solid material may be defined as the area under the stress-strain curve from beginning of stress that is greater than zero, to ultimate failure of the material.

Fracture toughness is an indication of the amount of stress required to propagate a pre-existing fracture. In other words, it is a measure of the ability of material to contain a crack to resist further fracture. There are various test methods for fracture toughness, such as for example, a V-shaped notch or a U-shaped notch in the material may be subjected to an impact from behind the notch. The resistance of the material for further fracture may be characterized.

The compressive strength toughness may equal to the ultimate compressive strength (UCS) divided by the maximum elastic compressive strength. Irrespective of the type of toughness measurement, the toughness value may be a consequence of cement hydration and chemical make-up and is thus a function of its composition. Also, a toughness ratio may be equal to the area under a plastic stress-strain curve divided by the area under the elastic stress-strain curve. Additionally, in some examples, toughness may be defined as the total areas of the stress-strain curve from loading until failure.

In particular examples, the mathematical model may relate measured values of various toughness definitions to the compositional attributes of a composition such as a cement to predict toughness for a new composition. Additionally, the mathematical models may allow for development of algorithms to facilitate tailoring cement slurries for improved perforation and fracturing performance.

For example, an existing composition may be modified to meet a target parameter/value such as toughness. Further, the model may allow analysis of hypothetical compositions and tailor components to meet target parameters, based on the analysis.

Quantifying toughness may be useful in tailoring cement sheath design for maximum perforation performance and fracturing efficiency. For example, the tailored sheath design may allow for a minimum compressive strength that satisfies life of the well requirements, while having maximum toughness. The higher the toughness of the cement, the lower the risk of fracture growth. If compressive strength exceeds certain limits, then the cement slurry may be over-designed/excessive for well requirements. The tailoring process should be directed to meet given requirements, such as for example, multiple stage fracturing with given perforation sizes, spatial patterns of perforation groups and spacing between the perforation groups.

In particular examples, cement sheaths may be designed such that the risk of unwanted fractures is reduced during loading (e.g., impact loading) such as during perforations. Perforation penetration into solid materials (e.g., cement sheaths and formations) may exponentially decrease with an increase in ultimate compressive strength (UCS). One method to quantify sudden impact toughness is via laboratory impact tests to measure efficacy of given cement sheath properties that correlates to their fracture toughness performance. Therefore, a goal of designing the cement sheath for optimum perforation performance may be to maintain the UCS as low as possible, while still meeting life of the well requirements, thus providing for maximum conservation of the perforation charge for penetration into the formation.

Additionally, the cement sheath may need maximum sudden impact toughness to minimize formation of fractures in the cement sheath such as unwanted fractures that may extend, for example, perpendicular or substantially perpendicular, from a perforation extending radially from the wellbore.

FIG. 1 illustrates an exemplary method for designing a composition/recipe based on a toughness value that is based on physico-chemical properties of the composition and test conditions, in accordance with particular examples of the present disclosure. In some examples, a computer may be implemented to design the composition.

At step 100, an inventory of components and physico-chemical properties of the inventory to design/tailor a composition/recipe may be reviewed/received. In some examples, the physico-chemical properties may be determined (e.g., calculated or measured). At step 102, an initial composition may be selected (e.g., historical design or its modifications) based on the inventory of components. This initial composition/recipe may serve as a starting point for tailored modification.

At step 104, physicochemical properties of the inventory and a model to predict a toughness, may be used to predict a toughness value of a cement composition. Models for compressive strength, thickening time, fluid loss, mixability, and other properties may also be used.

At step 106, the toughness of a cement composition may be predicted by at least one of exemplary Equations 1-4.

$$\text{toughness} = Af\left(\frac{w}{B}\right)g\left(\frac{Ca}{Si}, \frac{Al}{Si}\right)h\left(-\frac{1}{T}\right)p(P)k(PSD, \varphi) \quad \text{Eq. (1)}$$

where A is a constant, w/B is water to blend ratio of water to other components of the cement composition, f ( ), g ( ), h ( ), p ( ) and k ( ) are functions, Ca/Si is a calcium to silica ratio, Al/Si is an aluminum to silica ratio, T is temperature, P is pressure, PSD is a particle size distribution of particulates in the cement composition and φ is the shape factor of the particulates in the cement composition. The functions f ( ), g ( ), h ( ), p ( ) and k ( ) may be analytic expressions (e.g., a power law, exponential function, an algebraic expression), transcendental expressions, or may also be expressed as decision trees or neural nets.

$$\text{toughness} = A\left(\frac{w}{B}\right)^a\left(\frac{Ca}{Si}\right)^{b1}\left(\frac{Al}{Si}\right)^{b2}\exp\left(-\frac{E}{RT}\right)\exp\left(\frac{V_0 P}{RT_{ref}}\right) \quad \text{Eq. (2)}$$

where A, a, $b_1$, and $b_2$ are constants, w/B is water to blend ratio, Ca/Si is a calcium to silica ratio, Al/Si is an aluminum to silica ratio, E is activation energy, R is the universal gas constant, T is temperature, $V_0$ is the activation volume, P is the pressure, and $T_{ref}$ is a reference temperature.

One example form is given in the Eq. (2) and another form is given in Equation (3).

$$\text{toughness} = 61.75 \times \left(\frac{w}{b}\right)^{-0.896}\left(\frac{Ca}{Si}\right)^{-0.536} e^{-3387\left(\frac{1}{T_{ref}} - \frac{1}{T}\right)} \quad \text{Eq. (3)}$$

where w/B is water to blend ratio of water to other components of the cement composition, Ca/Si is a calcium to silica ratio, T is temperature, and $T_{ref}$ is a reference temperature. The total amount of Ca (or Si and Al) in the cement blend may be calculated with weight fractions using Equation 4, for example:

$$Ca = \sum_i w_i Ca_i \quad \text{Eq. (4)}$$

At step 108, requirements for a cement slurry such as the toughness, mixability, compressive strength, thickening time, fluid loss, rheology, at given conditions of temperature and pressure, may be determined, as desired per particular application. These requirements may be known/predetermined in some examples.

At step 110, the predicted toughness may be compared to the required toughness. If the prediction meets the requirement, then the designed composition with predicted toughness value is tested against other requirements such as for example, life-of-well requirements at step 112. These requirements may include compressive strength, tensile strength, elastic modulus, poison's ratio, cohesion, friction angle, thickening time, rheology, fluid loss, static gel time, and/or transition time.

If at step 114, the designed composition does not meet the toughness requirements or any other requirements, then the designed composition may be modified at step 116 until satisfactory results are achieved/thresholds are met. Modification of the composition may be achieved in various ways. For example, if the required toughness is higher than the current composition's toughness, using Eq. 3, the Ca/Si ratio may need to be reduced. From FIG. 7 it may be observed that Fly ash typically have lower Ca/Si compared to Portland Class G or H and Cement Kiln Dust (CKD).

Thus, replacing part of Portland and/or enhancer with fly ash material may enhance toughness.

Otherwise, at step 118, the designed composition is deemed tailored for the particular application and is used for a downhole operation such as cementing, for example. It should be noted that when the designed composition is adjusted, the water-to-blend ratio also changes, as it depends on the specific gravity and the weight fraction of individual materials.

In some examples, non-analytical model forms such as, for example, neural networks or other machine learning may also solve the toughness as a function of the water-to-blend mass ratio, the calcium-to-silica mass ratio, the alumina-to-silica ratio, pressure, particle size distribution, shape factor and the temperature of the composition relative to any reference temperature.

Figure 2:
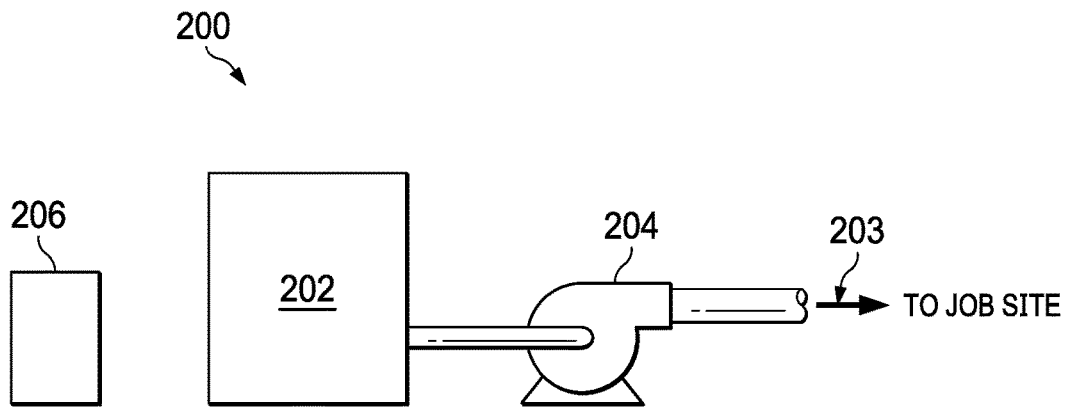
FIG. 2 illustrates a system for the preparation of a designed fluid(s) and subsequent delivery of the fluid to an application site, in accordance with examples of the present disclosure.

FIG. 2 illustrates a system 200 for the preparation of a designed fluid(s) and subsequent delivery of the fluid to an application site, in accordance with examples of the present disclosure. As shown, components may be mixed and/or stored in a vessel 202. The vessel 202 may be configured to contain and/or mix the components to produce or modify a designed composition 203 (e.g., a fluid, a cement). Non-limiting examples of the vessel 202 may include drums, barrels, tubs, bins, jet mixers, re-circulating mixers, and/or batch mixers. The designed composition 203 may then be moved (e.g., pumped via pumping equipment 204) to a location.

The system 200 may also include a computer 206 for calculating the required displacement efficiency as well as utilize the fluid design model to prepare the designed compositions/fluids. The computer 206 may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. The computer 206 may be any processor-driven device, such as, but not limited to, a personal computer, laptop computer, smartphone, tablet, handheld computer, dedicated processing device, and/or an array of computing devices. In addition to having a processor, the computer 206 may include a server, a memory, input/output ("I/O") interface(s), and a network interface. The memory may be any computer-readable medium, coupled to the processor, such as RAM, ROM, and/or a removable storage device for storing data and a database management system ("DBMS") to facilitate management of data stored in memory and/or stored in separate databases.

The computer 206 may also include display devices such as a monitor featuring an operating system, media browser, and the ability to run one or more software applications. Additionally, the computer 206 may include non-transitory computer-readable media. Non-transitory computer-readable media may include any instrumentality or aggregation of instrumentalities that may retain data and/or instructions for a period of time. The computer 206 may be used to perform calculations based on at least one of Equations 1-4 to provide a tailored composition.

Figure 3:
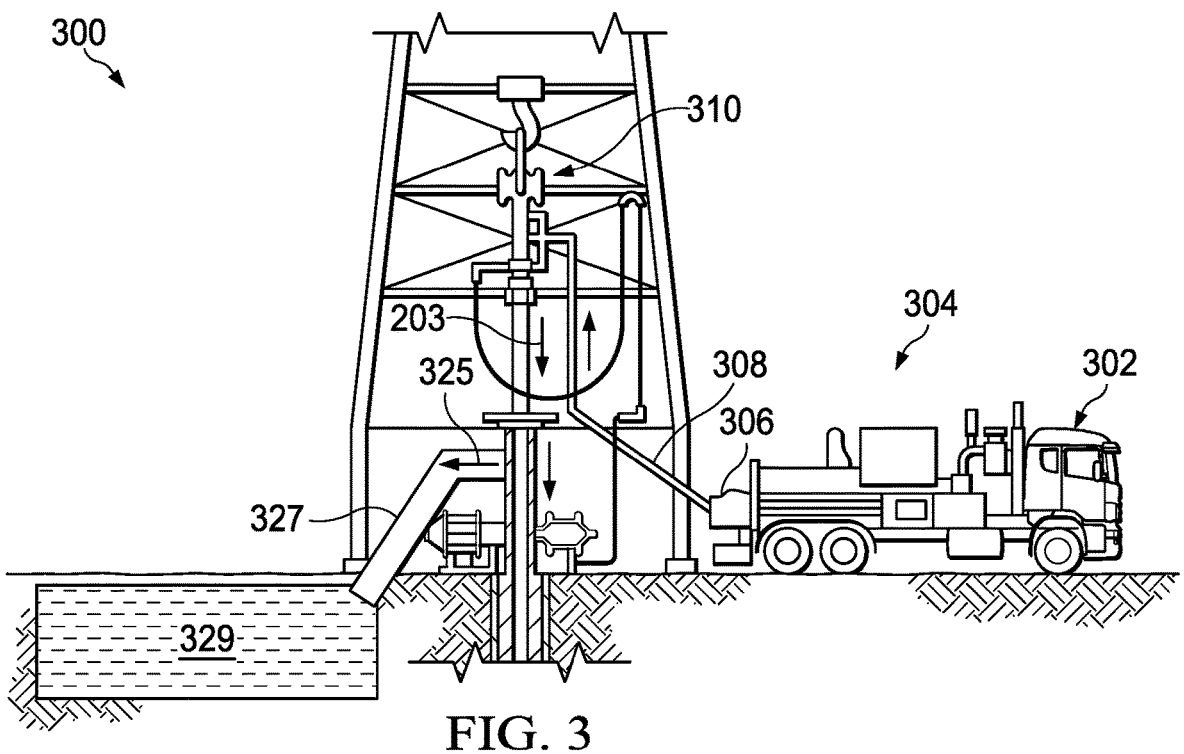
FIG. 3 illustrates a system that may be used in the placement of a cement composition, in accordance with examples of the present disclosure.

FIG. 3 illustrates a system 300 that may be used in the placement of a designed composition, in accordance with examples of the present disclosure. It should be noted that while FIG. 3 generally depicts a land-based operation, those skilled in the art will readily recognize that the principles described herein are equally applicable to subsea operations that employ floating or sea-based platforms and rigs, without departing from the scope of the disclosure.

The system 300 may include a cementing unit 302, which may include one or more cement trucks, for example. The cementing unit 302 may include mixing equipment 304 and pumping equipment 306. The cementing unit 302 may pump the designed composition 203, through a feed pipe 308 and to a cementing head 310 which conveys the composition 203 into a downhole environment.

Figure 4:
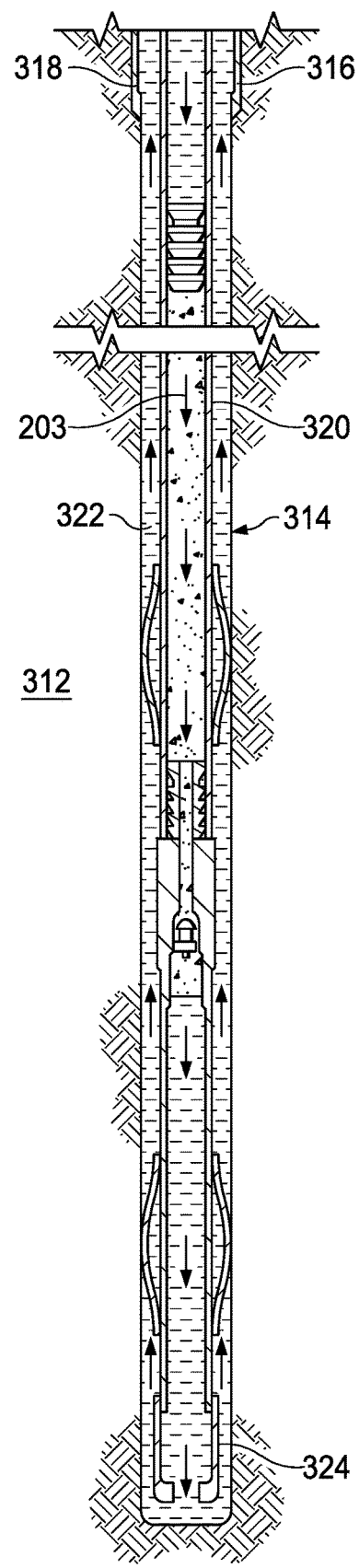
FIG. 4 illustrates the cement composition placed into a subterranean formation, in accordance with particular examples of the present disclosure.

With additional reference to FIG. 4, the composition 203 may be placed in a subterranean formation 312. A wellbore 314 may be drilled into the subterranean formation 312. While the wellbore 314 is shown generally extending vertically into the subterranean formation 312, the principles described herein are also applicable to wellbores that extend at an angle through subterranean formation 312, such as horizontal and slanted wellbores.

A first section 316 of casing may be inserted into the wellbore 314. The section 316 may be cemented in place by a cement sheath 318. A second section 320 of casing may also be disposed in the wellbore 314. A wellbore annulus 322 formed between the second section 320 and walls of the wellbore 314 and/or the first section 316.

The composition 203 may be pumped down the interior of the second section 320 of casing. The composition 203 may be allowed to flow down the interior of the casing through the casing shoe 324 at the bottom of the second section 320 and up around the second section 320 of casing into the wellbore annulus 322. As it is introduced, the composition 203 may displace other fluids 325, such as drilling fluids and/or spacer fluids that may be present in the interior of the casing and/or the wellbore annulus 322. At least a portion of the displaced fluids 325 may exit the wellbore annulus 322 via a flow line 327 and be deposited, for example, in one or more retention pits 329.

Other techniques may also be utilized for introduction of the composition 203. For example, reverse circulation techniques may be used that include introducing the composition 203 into the subterranean formation 312 via the wellbore annulus 322 instead of through the casing (e.g., section 320).

Figure 5:
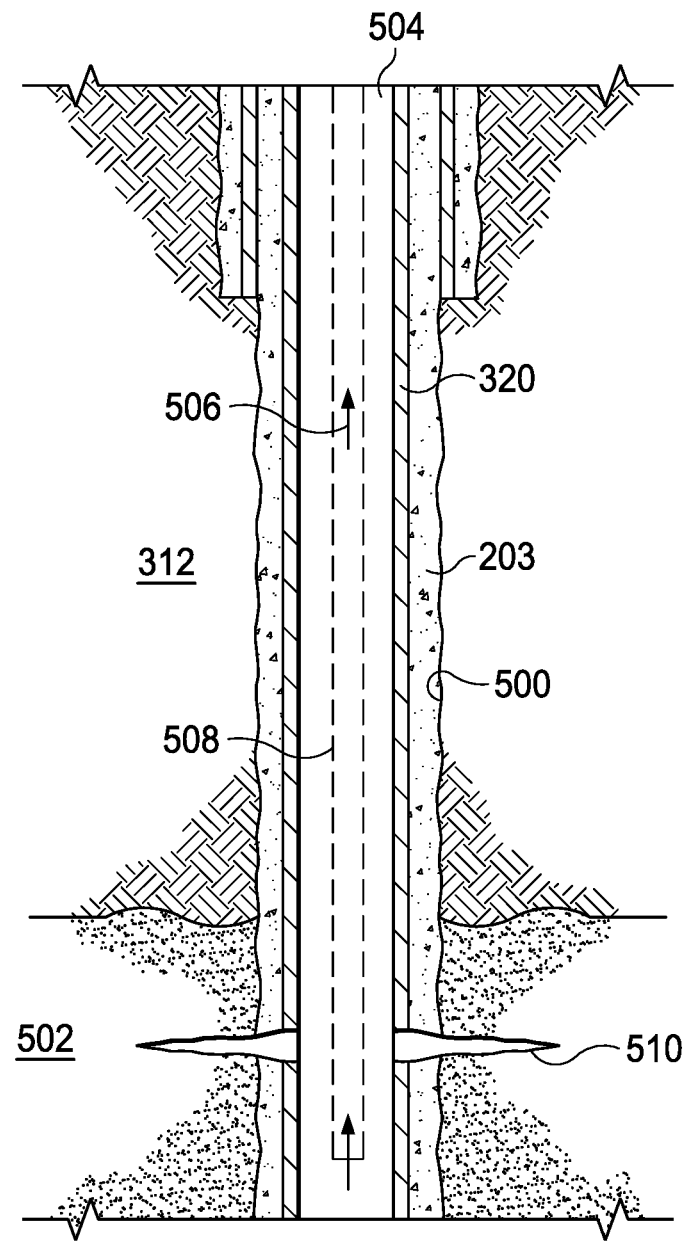
FIG. 5 illustrates the cement composition set within a subterranean formation to withstand undesirable fractures due to loading forces, in accordance with particular examples of the present disclosure.

With additional reference to FIG. 5, the composition 203 may then be allowed to set in the wellbore annulus 322, for example, to form a second cement sheath 500 that supports and positions the second section 320 of casing in the wellbore 314.

Hydrocarbons may then flow from a producing zone 502 of the subterranean formation 312 up through the second section 320 of casing and to a surface 504, as illustrated by arrows 506. Production tubing 508 may be disposed in the second section 320 of casing to produce the hydrocarbons.

In some examples, perforations 510 may extend into the subterranean formation 312. The set/hardened composition 203 may withstand impact loading during the perforation operations and prevent unwanted fractures that may extend perpendicularly or substantially perpendicular from the perforations 510.

Cement slurries described herein may generally include a hydraulic cement and water. A variety of hydraulic cements may be utilized in accordance with the present disclosure, including, but not limited to, those comprising calcium, aluminum, silicon, oxygen, iron, and/or sulfur, which set and harden by reaction with water. Suitable hydraulic cements may include, but are not limited to, Portland cements, pozzolana cements, gypsum cements, high alumina content cements, silica cements, and any combination thereof. In certain examples, the hydraulic cement may include a Portland cement. In some examples, the Portland cements may include Portland cements that are classified as Classes A, C, H, and G cements according to American Petroleum Institute, *API Specification for Materials and Testing for Well Cements*, API Specification 10, Fifth Ed., Jul. 1, 1990. In addition, hydraulic cements may include cements classified by American Society for Testing and Materials (ASTM) in C150 (Standard Specification for Portland Cement), C595 (Standard Specification for Blended Hydraulic Cement) or C1157 (Performance Specification for Hydraulic Cements) such as those cements classified as ASTM Type I, II, or III. The hydraulic cement may be included in the cement slurry in any amount suitable for a particular composition. Without limitation, the hydraulic cement may be included in the cement slurries in an amount in the range of from about 10% to about 80% by weight of dry blend in the cement slurry. For example, the hydraulic cement may be present in an amount ranging between any of and/or including any of about 10%, about 15%, about 20%, about 25%, about 30%, about 35%, about 40%, about 45%, about 50%, about 55%, about 60%, about 65%, about 70%, about 75%, or about 80% by weight of the cement slurries.

The water may be from any source provided that it does not contain an excess of compounds that may undesirably affect other components in the cement slurries. For example, a cement slurry may include fresh water or saltwater. Saltwater generally may include one or more dissolved salts therein and may be saturated or unsaturated as desired for a particular application. Seawater or brines may be suitable for use in some examples. Further, the water may be present in an amount sufficient to form a pumpable slurry. In certain examples, the water may be present in the cement slurry in an amount in the range of from about 33% to about 200% by weight of the cementitious materials. For example, the water cement may be present in an amount ranging between any of and/or including any of about 33%, about 50%, about 75%, about 100%, about 125%, about 150%, about 175%, or about 200% by weight of the cementitious materials. The cementitious materials referenced may include all components which contribute to the compressive strength of the cement slurry such as the hydraulic cement and supplementary cementitious materials, for example.

As mentioned above, the cement slurry may include supplementary cementitious materials. The supplementary cementitious material may be any material that contributes to the desired properties of the cement slurry. Some supplementary cementitious materials may include, without limitation, fly ash, blast furnace slag, silica fume, pozzolans, kiln dust, and clays, for example.

The cement slurry may include kiln dust as a supplementary cementitious material. "Kiln dust," as that term is used herein, refers to a solid material generated as a by-product of the heating of certain materials in kilns. The term "kiln dust" as used herein is intended to include kiln dust made as described herein and equivalent forms of kiln dust. Depending on its source, kiln dust may exhibit cementitious properties in that it can set and harden in the presence of water. Examples of suitable kiln dusts include cement kiln dust, lime kiln dust, and combinations thereof. Cement kiln dust may be generated as a by-product of cement production that is removed from the gas stream and collected, for example, in a dust collector. Usually, large quantities of cement kiln dust are collected in the production of cement that are commonly disposed of as waste. The chemical analysis of the cement kiln dust from various cement manufactures varies depending on a number of factors, including the particular kiln feed, the efficiencies of the cement production operation, and the associated dust collection systems. Cement kiln dust generally may include a variety of oxides, such as $SiO_2$, $Al_2O_3$, $Fe_2O_3$, CaO, MgO, $SO_3$, $Na_2O$, and $K_2O$. The chemical analysis of lime kiln dust from various lime manufacturers varies depending on several factors, including the particular limestone or dolomitic limestone feed, the type of kiln, the mode of operation of the kiln, the efficiencies of the lime production operation, and the associated dust collection systems. Lime kiln dust generally may include varying amounts of free lime and free magnesium, lime stone, and/or dolomitic limestone and a variety of oxides, such as $SiO_2$, $Al_2O_3$, $Fe_2O_3$, CaO, MgO, $SO_3$, $Na_2O$, and $K_2O$, and other components, such as chlorides. A cement kiln dust may be added to the cement slurry prior to, concurrently with, or after activation. Cement kiln dust may include a partially calcined kiln feed which is removed from the gas stream and collected in a dust collector during the manufacture of cement. The chemical analysis of CKD from various cement manufactures varies depending on a number of factors, including the particular kiln feed, the efficiencies of the cement production operation, and the associated dust collection systems. CKD generally may comprise a variety of oxides, such as $SiO_2$, $Al_2O_3$, $Fe_2O_3$, CaO, MgO, $SO_3$, $Na_2O$, and $K_2O$. The CKD and/or lime kiln dust may be included in examples of the cement slurry in an amount suitable for a particular application.

In some examples, the cement slurry may further include one or more of slag, natural glass, shale, amorphous silica, or metakaolin as a supplementary cementitious material. Slag is generally a granulated, blast furnace by-product from the production of cast iron including the oxidized impurities found in iron ore. The cement may further include shale. A variety of shales may be suitable, including those including silicon, aluminum, calcium, and/or magnesium. Examples of suitable shales include vitrified shale and/or calcined shale. In some examples, the cement slurry may further include amorphous silica as a supplementary cementitious material. Amorphous silica is a powder that may be included in embodiments to increase cement compressive strength. Amorphous silica is generally a byproduct of a ferrosilicon production process, wherein the amorphous silica may be formed by oxidation and condensation of gaseous silicon suboxide, SiO, which is formed as an intermediate during the process In some examples, the cement slurry may further include a variety of fly ashes as a supplementary cementitious material which may include fly ash classified as Class C, Class F, or Class N fly ash according to American Petroleum Institute, API Specification for Materials and Testing for Well Cements, API Specification 10, Fifth Ed., Jul. 1, 1990. In some examples, the cement slurry may further include zeolites as supplementary cementitious materials. Zeolites are generally porous alumino-silicate minerals that may be either natural or synthetic. Synthetic zeolites are based on the same type of structural cell as natural zeolites and may comprise aluminosilicate hydrates. As used herein, the term "zeolite" refers to all natural and synthetic forms of zeolite.

Where used, one or more of the aforementioned supplementary cementitious materials may be present in the cement slurry. For example, without limitation, one or more supplementary cementitious materials may be present in an amount of about 0.1% to about 80% by weight of the cement slurry. For example, the supplementary cementitious materials may be present in an amount ranging between any of and/or including any of about 0.1%, about 10%, about 20%, about 30%, about 40%, about 50%, about 60%, about 70%, or about 80% by weight of the cement.

In some examples, the cement slurry may further include hydrated lime. As used herein, the term "hydrated lime" will be understood to mean calcium hydroxide. In some embodiments, the hydrated lime may be provided as quicklime (calcium oxide) which hydrates when mixed with water to form the hydrated lime. The hydrated lime may be included in examples of the cement slurry, for example, to form a hydraulic composition with the supplementary cementitious components. For example, the hydrated lime may be included in a supplementary cementitious material-to-hydrated-lime weight ratio of about 10:1 to about 1:1 or 3:1 to about 5:1. Where present, the hydrated lime may be included in the set cement slurry in an amount in the range of from about 10% to about 100% by weight of the cement slurry, for example. In some examples, the hydrated lime may be present in an amount ranging between any of and/or including any of about 10%, about 20%, about 40%, about 60%, about 80%, or about 100% by weight of the cement slurry. In some examples, the cementitious components present in the cement slurry may consist essentially of one or more supplementary cementitious materials and the hydrated lime. For example, the cementitious components may primarily comprise the supplementary cementitious materials and the hydrated lime without any additional components (e.g., Portland cement, fly ash, slag cement) that hydraulically set in the presence of water.

Lime may be present in the cement slurry in several; forms, including as calcium oxide and or calcium hydroxide or as a reaction product such as when Portland cement reacts with water. Alternatively, lime may be included in the cement slurry by amount of silica in the cement slurry. A cement slurry may be designed to have a target lime to silica weight ratio. The target lime to silica ratio may be a molar ratio, molal ratio, or any other equivalent way of expressing a relative amount of silica to lime. Any suitable target time to silica weight ratio may be selected including from about 10/90 lime to silica by weight to about 40/60 lime to silica by weight. Alternatively, about 10/90 lime to silica by weight to about 20/80 lime to silica by weight, about 20/80 lime to silica by weight to about 30/70 lime to silica by weight, or about 30/70 lime to silica by weight to about 40/63 lime to silica by weight.

Other additives suitable for use in subterranean cementing operations also may be included in embodiments of the cement slurry. Examples of such additives include, but are not limited to: weighting agents, lightweight additives, gas-generating additives, mechanical-property-enhancing additives, lost-circulation materials, filtration-control additives, fluid-loss-control additives, defoaming agents, foaming agents, thixotropic additives, and combinations thereof. In embodiments, one or more of these additives may be added to the cement slurry after storing but prior to the placement of a cement slurry into a subterranean formation. In some examples, the cement slurry may further include a dispersant. Examples of suitable dispersants include, without limitation, sulfonated-formaldehyde-based dispersants (e.g., sulfonated acetone formaldehyde condensate) or polycarboxylated ether dispersants. In some examples, the dispersant may be included in the cement slurry in an amount in the range of from about 0.01% to about 5% by weight of the cementitious materials. In specific examples, the dispersant may be present in an amount ranging between any of and/or including any of about 0.010%, about 0.10%, about 0.5%, about 1%, about 2%, about 3%, about 4%, or about 5% by weight of the cementitious materials.

In some examples, the cement slurry may further include a set retarder. A broad variety of set retarders may be suitable for use in the cement slurries. For example, the set retarder may comprise phosphonic acids, such as ethylenediamine tetra(methylene phosphonic acid), diethylenetriamine penta (methylene phosphonic acid), etc.; lignosulfonates, such as sodium lignosulfonate, calcium lignosulfonate, etc.; salts such as stannous sulfate, lead acetate, monobasic calcium phosphate, organic acids, such as citric acid, tartaric acid, etc.; cellulose derivatives such as hydroxyl ethyl cellulose (HEC) and carboxymethyl hydroxyethyl cellulose (CMHEC); synthetic co- or ter-polymers comprising sulfonate and carboxylic acid groups such as sulfonate-functionalized acrylamide-acrylic acid co-polymers; borate compounds such as alkali borates, sodium metaborate, sodium tetraborate, potassium pentaborate; derivatives thereof, or mixtures thereof. Examples of suitable set retarders include, among others, phosphonic acid derivatives. Generally, the set retarder may be present in the cement slurry in an amount sufficient to delay the setting for a desired time. In some examples, the set retarder may be present in the cement slurry in an amount in the range of from about 0.01% to about 10% by weight of the cementitious materials. In specific examples, the set retarder may be present in an amount ranging between any of and/or including any of about 0.01%, about 0.10%, about 1%, about 2%, about 4%, about 6%, about 8%, or about 10% by weight of the cementitious materials.

In some examples, the cement slurry may further include an accelerator. A broad variety of accelerators may be suitable for use in the cement slurries. For example, the accelerator may include, but are not limited to, aluminum sulfate, alums, calcium chloride, calcium nitrate, calcium nitrite, calcium formate, calcium sulphoaluminate, calcium sulfate, gypsum-hemihydrate, sodium aluminate, sodium carbonate, sodium chloride, sodium silicate, sodium sulfate, ferric chloride, or a combination thereof. In some examples, the accelerators may be present in the cement slurry in an amount in the range of from about 0.01% to about 10% by weight of the cementitious materials. In specific examples, the accelerators may be present in an amount ranging between any of and/or including any of about 0.01%, about 0.1%, about 1%, about 2%, about 4%, about 6%, about 8%, or about 10% by weight of the cementitious materials.

Cement slurries generally should have a density suitable for a particular application. By way of example, the cement slurry may have a density in the range of from about 8 pounds per gallon ("ppg") (959 kg/m$^3$) to about 20 ppg (2397 kg/m$^3$), or about 8 ppg to about 12 ppg (1437. kg/m$^3$), or about 12 ppg to about 16 ppg (1917.22 kg/m$^3$), or about 16 ppg to about 20 ppg, or any ranges therebetween. Examples of the cement slurry may be foamed or unfoamed or may comprise other means to reduce their densities, such as hollow microspheres, low-density elastic beads, or other density-reducing additives known in the art.

The cement slurries disclosed herein may be used in a variety of subterranean applications, including primary and remedial cementing. The cement slurries may be introduced into a subterranean formation and allowed to set. In primary cementing applications, for example, the cement slurries may be introduced into the annular space between a conduit located in a wellbore and the walls of the wellbore (and/or a larger conduit in the wellbore), wherein the wellbore penetrates the subterranean formation. The cement slurry may be allowed to set in the annular space to form an annular sheath of hardened cement. The cement slurry may form a barrier that prevents the migration of fluids in the wellbore. The cement slurry may also, for example, support the conduit in the wellbore. In remedial cementing applications, the cement slurry may be used, for example, in squeeze cementing operations or in the placement of cement plugs. By way of example, the cement slurry may be placed in a wellbore to plug an opening (e.g., a void or crack) in the formation, in a gravel pack, in the conduit, in the cement sheath, and/or between the cement sheath and the conduit (e.g., a micro annulus).

The following example is intended to facilitate an understanding of the techniques as described herein.

Example

To build a mathematical model for toughness, test data from 25 different cement compositions was used. These compositions covered a temperature range of 140° F. to 240° F. and a density range of 9 pounds per gallon (ppg) to 15.8 ppg. Blend materials were made up of 17 different Portland cements, 4 cement kiln dust, 3 Pozzolanic materials, 7 Fly Ashes, 2 Silicalites, 2 glass beads and Crystalline Silica. Measurements of axial stress and strain were taken during static compression tests on each composition, to calculate toughness as an area under the curve. The tests were conducted until sample failure is observed so that the complete stress—strain curve is available for calculations.

Physico-chemical properties of the blend materials used in 25 compositions were extracted. Mass averaged values of Ca and Si were calculated for the blend portion of the compositions to determine Eq. 1.

Figure 6:
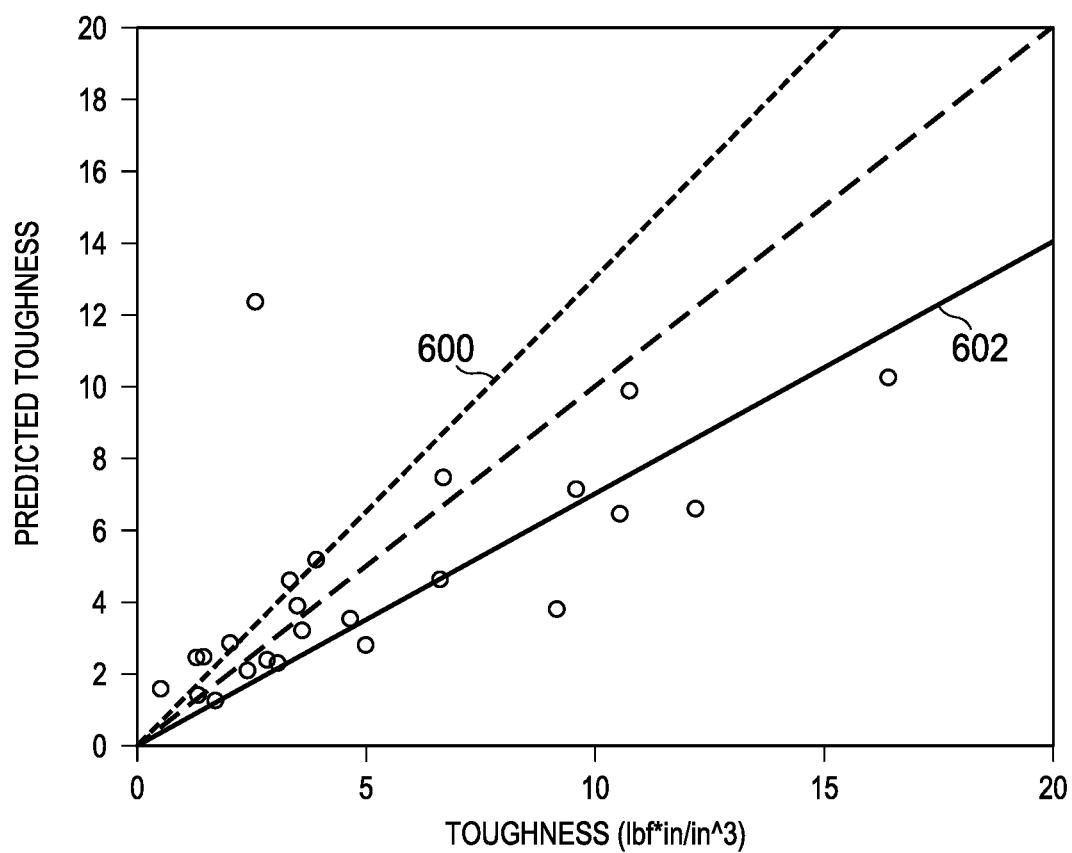
FIG. 6 illustrates a parity plot of calculated and predicting toughness values, in accordance with particular examples of the present disclosure.

FIG. 6 illustrates a parity plot of measured and predicted toughness, in accordance with techniques as described herein. A power law form for (w/blend), (Ca/Si) and exponential form for 1/T may be used. However, other mathematical forms may also be employed. Examples include exponential, linear or quadratic forms for (w/blend), (Ca/Si). As illustrated, ±30% bounds are also shown indicated by boundary 600 (+30%) and boundary 602 (−30%). Alternately, a non-analytical approach (e.g., neural networks or another machine learning model) may also describe the toughness as a function of the w/blend, the temperature of the composition, and the Ca/Si. Table 1 illustrates predictions based on the techniques as described herein.

TABLE 1

Predictions of Toughness for Three Example Compositions.

| | Mass Fractions | | | | | |
|---|---|---|---|---|---|---|
| Sample No. | Class H portland | Volcanic glass | Fly Ash | CaO/ SiO$_2$ | Water/ Blend | Toughness |
| 1 | 1 | 0 | 0 | 4.23 | 0.809 | 8.8 |
| 2 | 0.5 | 0 | 0.5 | 1.28 | 0.691 | 19.3 |
| 3 | 0.6 | 0.2 | 0.2 | 1.42 | 0.708 | 17.9 |

For the predictions, density and temperature are maintained at 13.5 ppg and 180° F. respectively for all three compositions. For the selected materials, the CaO and SiO$_2$ values are as shown in Table 2. In particular examples, the addition of pozzolanic materials has a positive impact on the toughness. A larger toughness value indicates increased toughness.

TABLE 2

CaO and SiO$_2$ properties of materials used in example compositions.

| Material | CaO | SiO$_2$ |
|---|---|---|
| Class H portland | 44.583 | 10.54 |
| Volcanic glass | 0.007 | 38.42 |
| Fly Ash | 1.601 | 25.56 |

Figure 7:
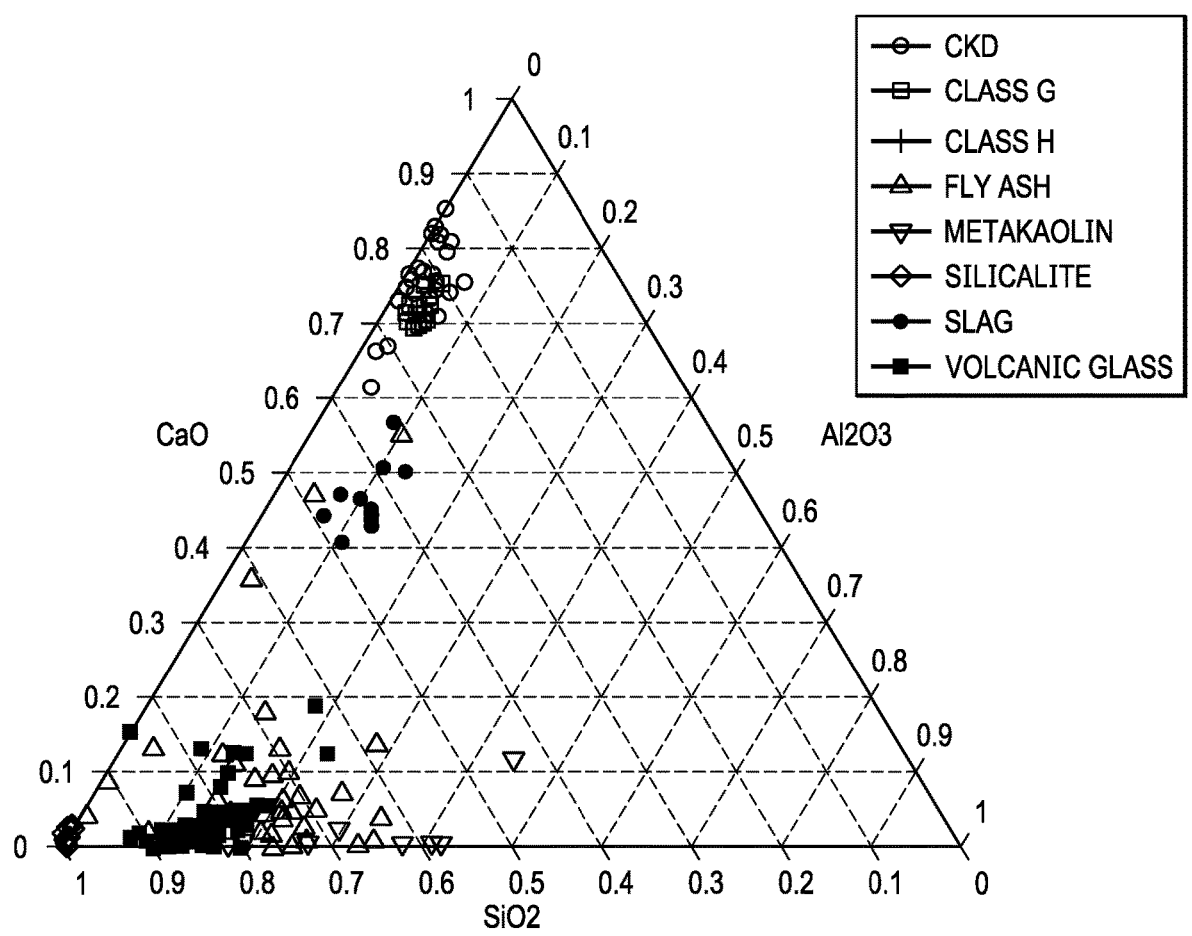
FIG. 7 illustrates a ternary diagram, in accordance with examples of the present disclosure.

FIG. 7 illustrates a ternary diagram, in accordance with examples of the present disclosure. The ternary diagram illustrates relative composition of three constituents that make up a material. The three constituents add up to 1 (or 100%). This plot shows the composition of various material types in terms of their constituents: silica, calcium, and alumina. For example, Silicalite is silica rich material and on the ternary diagram, various sources of Silicalite are situated around 100% silica content.

Accordingly, the techniques of the present disclosure may be employed to assess/evaluate an existing cement composition or design a new cement composition for a target toughness value. The systems and methods may include any of the various features disclosed herein, including one or more of the following statements.

Statement 1. A method comprises (a) selecting at least a cementitious material and concentration thereof and a water and concentration thereof to form a cement slurry recipe; (b) calculating a toughness for the cement slurry recipe using a toughness model wherein the toughness model comprises an input of physicochemical properties of components of the cement slurry recipe; (c) comparing the toughness of the cement slurry recipe to a toughness requirement; (d) repeating steps (a)-(c) if the calculated toughness of the cement slurry recipe does not meet or exceed the toughness requirement, wherein each repeated step of selecting comprises selecting different concentrations and/or different chemical identities for at least the cementitious material and/or water than previously selected; and (e) preparing a cement slurry based on the cement slurry recipe, the cement slurry including a toughness that meets or exceeds the toughness requirement.

Statement 2. The method of the statement 1, wherein the toughness model comprises an equation of the following form:

$$\text{toughness} = Af\left(\frac{w}{B}\right)g\left(\frac{Ca}{Si}, \frac{Al}{Si}\right)h\left(-\frac{1}{T}\right)p(P)k(PSD, \varphi)$$

where A is a constant, w/B is water to blend ratio of water to other components of the cement slurry recipe, f ( ), g ( ), h ( ), p ( ) and k ( ) are functions, Ca/Si is a calcium to silica ratio, Al/Si is an aluminum to silica ratio, T is temperature, P is pressure, PSD is a particle size distribution of particulates in the cement composition and cp is the shape factor of the particulates in the cement slurry recipe.

Statement 3. The method of the statement 2, wherein f ( ), g ( ), h ( ), p ( ) and k ( ) are at least one of a power law, an exponential function, an algebraic expression, a transcendental expression, a decision trees, or a neural net.

Statement 4. The method of any of the preceding statements, wherein the toughness model comprises an equation of the following form:

$$\text{toughness} = A\left(\frac{w}{B}\right)^a\left(\frac{Ca}{Si}\right)^{b1}\left(\frac{Al}{Si}\right)^{b2}\exp\left(-\frac{E}{RT}\right)\exp\left(\frac{V_0 P}{RT_{ref}}\right)$$

where A, a, $b_1$, and $b_2$ are constants, w/B is water to blend ratio, Ca/Si is a calcium to silica ratio, Al/Si is an aluminum to silica ratio, E is activation energy, R is universal gas constant, T is temperature, $V_0$ is activation volume, P is pressure, and $T_{ref}$ is reference temperature.

Statement 5. The method of any of the preceding statements, wherein the toughness model comprises an equation of the following form:

$$\text{toughness} = 61.75 \times \left(\frac{w}{b}\right)^{-0.896} \left(\frac{\text{Ca}}{\text{Si}}\right)^{-0.536} e^{-3387\left(\frac{1}{T_{ref}} - \frac{1}{T}\right)}$$

where w/B is water to blend ratio of water to other components of the cement composition, Ca/Si is a calcium to silica ratio, T is temperature, and $T_{ref}$ is a reference temperature.

Statement 6. The method of any of the preceding statements, wherein the toughness requirement is at least one toughness selected from the group consisting of fracture toughness, sudden impact toughness, compressive strength toughness, secant toughness, and combinations thereof.

Statement 7. The method of any of the preceding statements, wherein each repeated step of selecting comprises selecting a disparate water-to-blend mass ratio.

Statement 8. The method of any of the preceding statements, wherein each repeated step of selecting comprises selecting a disparate calcium-to-silica ratio.

Statement 9. The method of any of the preceding statements, wherein each repeated step of selecting comprises selecting a disparate alumina-to-silica ratio.

Statement 10. The method of any of the preceding statements, wherein the physicochemical properties of components of the cement slurry recipe comprise Ca/Si is a calcium to silica ratio, Al/Si is an aluminum to silica ratio, or combinations thereof.

Statement 11. A method comprises generating a cement slurry recipe using a toughness model wherein the toughness model comprises an input of physicochemical properties of components of the cement slurry recipe, such that a calculated toughness of the cement slurry recipe using the toughness model meets or exceeds the toughness requirement; and preparing a cement slurry based on the cement slurry recipe.

Statement 12. The method of any of the statements 11, wherein the toughness model comprises an equation of the following form:

$$\text{toughness} = Af\left(\frac{w}{B}\right)g\left(\frac{\text{Ca}}{\text{Si}}, \frac{\text{Al}}{\text{Si}}\right)h\left(-\frac{1}{T}\right)p(P)k(PSD, \varphi)$$

where A is a constant, w/B is water to blend ratio of water to other components of the cement slurry recipe, f ( ), g ( ), h ( ), p ( ) and k ( ) are functions, Ca/Si is a calcium to silica ratio, Al/Si is an aluminum to silica ratio, T is temperature, P is pressure, PSD is a particle size distribution of particulates in the cement composition and φ is the shape factor of the particulates in the cement slurry recipe.

Statement 13. The method of the statement 11 or the statement 12, wherein f ( ), g ( ), h ( ), p ( ) and k ( ) are at least one of a power law, an exponential function, an algebraic expression, a transcendental expression, a decision trees, or a neural net.

Statement 14. The method of any of the statements 11-13, wherein the toughness model comprises an equation of the following form:

$$\text{toughness} = A\left(\frac{w}{B}\right)^a \left(\frac{\text{Ca}}{\text{Si}}\right)^{b1} \left(\frac{\text{Al}}{\text{Si}}\right)^{b2} \exp\left(-\frac{E}{RT}\right) \exp\left(\frac{V_0 P}{RT_{ref}}\right)$$

where A, a, $b_1$, and $b_2$ are constants, w/B is water to blend ratio, Ca/Si is a calcium to silica ratio, Al/Si is an aluminum to silica ratio, E is activation energy, R is universal gas constant, T is temperature, $V_0$ is activation volume, P is pressure, and $T_{ref}$ is reference temperature.

Statement 15. The method of any of the statements 11-14, wherein the toughness model comprises an equation of the following form:

$$\text{toughness} = 61.75 \times \left(\frac{w}{b}\right)^{-0.896} \left(\frac{\text{Ca}}{\text{Si}}\right)^{-0.536} e^{-3387\left(\frac{1}{T_{ref}} - \frac{1}{T}\right)}$$

where w/B is water to blend ratio of water to other components of the cement composition, Ca/Si is a calcium to silica ratio, T is temperature, and $T_{ref}$ is a reference temperature.

Statement 16. The method of any of the statements 11-15, wherein the toughness requirement is at least one toughness selected from the group consisting of fracture toughness, sudden impact toughness, compressive strength toughness, secant toughness, and combinations thereof.

Statement 17. The method of any of the statements 11-16, wherein generating a cement slurry recipe using the toughness model comprises selecting a water-to-blend mass ratio.

Statement 18. The method of any of the statements 11-17, wherein generating a cement slurry recipe using the toughness model comprises selecting a calcium-to-silica ratio.

Statement 19. The method of any of the statements 11-18, wherein generating a cement slurry recipe using the toughness model comprises selecting an alumina-to-silica mass ratio.

Statement 20. The method of any of the statements 11-19, wherein the physicochemical properties of components of the cement slurry recipe comprise Ca/Si is a calcium to silica ratio, Al/Si is an aluminum to silica ratio, or combinations thereof.

The preceding description provides various examples of the systems and methods of use disclosed herein which may contain different method steps and alternative combinations of components. It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A method for designing a composition, the method comprising:
   (a) selecting at least a cementitious material and concentration thereof and a water and concentration thereof to form a cement slurry recipe;
   (b) calculating a toughness for the cement slurry recipe using a toughness model wherein the toughness model comprises an input of physicochemical properties of components of the cement slurry recipe, wherein the toughness model comprises an equation of the following form:

$$\text{toughness} = Af\left(\frac{w}{B}\right)g\left(\frac{Ca}{Si}, \frac{Al}{Si}\right)h\left(-\frac{1}{T}\right)p(P)k(PSD, \varphi)$$

where A is a constant, w/B is water to blend ratio of water to other components of the cement slurry recipe, f ( ), g ( ), h ( ), p ( ) and k ( ) are functions, Ca/Si is a calcium to silica ratio, Al/Si is an aluminum to silica ratio, T is temperature, P is pressure, PSD is a particle size distribution of particulates in the cement composition and $\varphi$ is the shape factor of the particulates in the cement slurry recipe;
   (c) comparing the toughness of the cement slurry recipe to a toughness requirement;
   (d) repeating steps (a)-(c) if the calculated toughness of the cement slurry recipe does not meet or exceed the toughness requirement, wherein each repeated step of selecting comprises selecting different concentrations and/or different chemical identities for at least the cementitious material and/or water than previously selected; and
   (e) preparing a cement slurry based on the cement slurry recipe, the cement slurry including a toughness that meets or exceeds the toughness requirement.

2. The method of claim 1, wherein f ( ), g ( ), h ( ), p ( ), and k ( ) are at least one of a power law, an exponential function, an algebraic expression, a transcendental expression, a decision trees, or a neural net.

3. The method of claim 1, wherein the toughness model comprises an equation of the following form:

$$\text{toughness} = 61.75 \times \left(\frac{w}{b}\right)^{-0.896}\left(\frac{Ca}{Si}\right)^{-0.536} e^{-3387\left(\frac{1}{T_{ref}} - \frac{1}{T}\right)}$$

where w/B is water to blend ratio of water to other components of the cement composition, Ca/Si is a calcium to silica ratio, T is temperature, and $T_{ref}$ is a reference temperature.

4. The method of claim 1, wherein the toughness requirement is at least one toughness selected from the group consisting of fracture toughness, sudden impact toughness, compressive strength toughness, secant toughness, and combinations thereof.

5. The method of claim 1, wherein each repeated step of selecting comprises selecting a different water-to-blend mass ratio.

6. The method of claim 1, wherein each repeated step of selecting comprises selecting a different calcium-to-silica ratio.

7. The method of claim 1, wherein each repeated step of selecting comprises selecting a different alumina-to-silica ratio.

8. The method of claim 1, wherein the physicochemical properties of components of the cement slurry recipe comprise Ca/Si is a calcium to silica ratio, Al/Si is an aluminum to silica ratio, or combinations thereof.

9. The method of claim 8, wherein the toughness requirement is at least one toughness selected from the group consisting of fracture toughness, sudden impact toughness, compressive strength toughness, secant toughness, and combinations thereof.

10. A method comprising:
    generating a cement slurry recipe using a toughness model wherein the toughness model comprises an input of physicochemical properties of components of the cement slurry recipe, such that a calculated toughness of the cement slurry recipe using the toughness model meets or exceeds the toughness requirement, wherein the toughness model comprises an equation of the following form:

$$\text{toughness} = Af\left(\frac{w}{B}\right)g\left(\frac{Ca}{Si}, \frac{Al}{Si}\right)h\left(-\frac{1}{T}\right)p(P)k(PSD, \varphi)$$

where A is a constant, w/B is water to blend ratio of water to other components of the cement slurry recipe, f ( ), g ( ), h ( ), p ( ) and k ( ) are functions, Ca/Si is a calcium to silica ratio, Al/Si is an aluminum to silica ratio, T is temperature, P is pressure, PSD is a particle size distribution of particulates in the cement composition and $\varphi$ is the shape factor of the particulates in the cement slurry recipe; and preparing a cement slurry based on the cement slurry recipe.

11. The method of claim 10, wherein f ( ), g ( ), h ( ), p ( ) and k ( ) are at least one of a power law, an exponential function, an algebraic expression, a transcendental expression, a decision trees, or a neural net.

12. The method of claim 10, wherein the toughness model comprises an equation of the following form:

$$\text{toughness} = 61.75 \times \left(\frac{w}{b}\right)^{-0.896} \left(\frac{Ca}{Si}\right)^{-0.536} e^{-3387\left(\frac{1}{T_{ref}} - \frac{1}{T}\right)}$$

where w/B is water to blend ratio of water to other components of the cement composition, Ca/Si is a calcium to silica ratio, T is temperature, and $T_{ref}$ is a reference temperature.

13. The method of claim 10, wherein generating a cement slurry recipe using the toughness model comprises selecting a water-to-blend mass ratio.

14. The method of claim 10, wherein generating a cement slurry recipe using the toughness model comprises selecting a calcium-to-silica ratio.

15. The method of claim 10, wherein generating a cement slurry recipe using the toughness model comprises selecting an alumina-to-silica mass ratio.

16. The method of claim 10, wherein the physicochemical properties of components of the cement slurry recipe comprise Ca/Si is a calcium to silica ratio, Al/Si is an aluminum to silica ratio, or combinations thereof.

17. A method for designing a composition, the method comprising:
   (a) selecting at least a cementitious material and concentration thereof and a water and concentration thereof to form a cement slurry recipe;
   (b) calculating a toughness for the cement slurry recipe using a toughness model wherein the toughness model comprises an input of physicochemical properties of components of the cement slurry recipe, wherein the toughness model comprises an equation of the following form:

$$\text{toughness} = A\left(\frac{w}{B}\right)^a \left(\frac{Ca}{Si}\right)^{b1} \left(\frac{Al}{Si}\right)^{b2} \exp\left(-\frac{E}{RT}\right) \exp\left(\frac{V_0 P}{RT_{ref}}\right)$$

where A, a, $b_1$, and $b_2$ are constants, w/B is water to blend ratio, Ca/Si is a calcium to silica ratio, Al/Si is an aluminum to silica ratio, E is activation energy, R is universal gas constant, T is temperature, $V_0$ is activation volume, P is pressure, and $T_{ref}$ is reference temperature;
   (c) comparing the toughness of the cement slurry recipe to a toughness requirement;
   (d) repeating steps (a)-(c) if the calculated toughness of the cement slurry recipe does not meet or exceed the toughness requirement, wherein each repeated step of selecting comprises selecting different concentrations and/or different chemical identities for at least the cementitious material and/or water than previously selected; and
   (e) preparing a cement slurry based on the cement slurry recipe, the cement slurry including a toughness that meets or exceeds the toughness requirement.

18. A method comprising:
generating a cement slurry recipe using a toughness model wherein the toughness model comprises an input of physicochemical properties of components of the cement slurry recipe, such that a calculated toughness of the cement slurry recipe using the toughness model meets or exceeds the toughness requirement, wherein the toughness model comprises an equation of the following form:

$$\text{toughness} = A\left(\frac{w}{B}\right)^a \left(\frac{Ca}{Si}\right)^{b1} \left(\frac{Al}{Si}\right)^{b2} \exp\left(-\frac{E}{RT}\right) \exp\left(\frac{V_0 P}{RT_{ref}}\right)$$

where A, a, $b_1$, and $b_2$ are constants, w/B is water to blend ratio, Ca/Si is a calcium to silica ratio, Al/Si is an aluminum to silica ratio, E is activation energy, R is universal gas constant, T is temperature, $V_0$ is activation volume, P is pressure, and $T_{ref}$ is reference temperature; and
preparing a cement slurry based on the cement slurry recipe.

* * * * *